United States Patent [19]
Riondel et al.

[11] Patent Number: 5,998,646
[45] Date of Patent: Dec. 7, 1999

[54] UNSATURATED ORGANOMETALLIC COMPOUNDS DERIVED FROM TITANIUM AND PROCESS FOR THEIR PREPARATION

[75] Inventors: Alain Riondel, Forbach; Michel Camail, Brignoles; Andre Margaillan, Gareoult; Jean-Louis Vernet, La Farlede; Marie Humbert, Marseilles, all of France

[73] Assignee: Elf Atochem S.A., Paris-La-Defense, France

[21] Appl. No.: 09/185,499

[22] Filed: Nov. 4, 1998

Related U.S. Application Data

[63] Continuation-in-part of application No. 08/915,931, Aug. 21, 1997, abandoned.

[30] Foreign Application Priority Data

Aug. 22, 1996 [FR] France ................................. 96/10372

[51] Int. Cl.$^6$ ...................................................... C07F 7/28
[52] U.S. Cl. ............................................................. 556/55
[58] Field of Search ................................................. 556/55

[56] References Cited

U.S. PATENT DOCUMENTS

| | | | |
|---|---|---|---|
| 2,940,957 | 6/1960 | Herman | 260/78.5 |
| 3,337,391 | 8/1967 | Clayton et al. | 161/170 |

FOREIGN PATENT DOCUMENTS

| | | |
|---|---|---|
| 0452882 | 10/1991 | European Pat. Off. . |
| 3137840 | 3/1983 | Germany . |
| 3224927 | 1/1984 | Germany . |
| 3224928 | 1/1984 | Germany . |

*Primary Examiner*—Porfirio Nazario-Gonzalez
*Attorney, Agent, or Firm*—Millen, White, Zelano & Branican, P.C.

[57] ABSTRACT

These compounds are denoted by the formula (I):

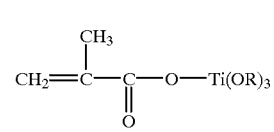

in which R denotes a tert-butyl, tert-amyl or 2-ethylhexyl radical.

To prepare them, methacrylic acid is reacted with a tetraalkoxytitanium Ti(OR)$_4$, where R=isopropyl or tert-butyl, to obtain a corresponding compound (I), or with Ti(OR) (OtAm)$_3$, where R=isopropyl or tert-butyl and tAm=tert-amyl, to obtain a compound (I) with R=tert-amyl, the compounds (I) with R=isopropyl or tert-butyl furthermore denoting intermediate synthesis products which can be reacted with tert-amyl alcohol or with 2-ethylhexanol, to obtain a compound (I) in which R denotes tert-amyl or 2-ethylhexyl respectively.

9 Claims, No Drawings

UNSATURATED ORGANOMETALLIC COMPOUNDS DERIVED FROM TITANIUM AND PROCESS FOR THEIR PREPARATION

CROSS-REFERENCE TO RELATED APPLICATION

This application is a continuation-in-part of application Ser. No. 08/915,931 entitled "Unsaturated Organometallic Compounds Derived from Titanium and Process for Their Production" by Diondel et al. filed Aug. 21, 1997, now abandoned. In addition, this application is related to commonly assigned application Ser. No. 08/915,799, entitled "New (Meth)acrylic Resin Compositions for Marine Antifouling Paints and Corresponding Paint Compositions" by Vanhoye et al. filed Aug. 21, 1997, based on French priority application 96/10374 filed Aug. 22, 1996, incorporated by reference herein.

FIELD OF THE INVENTION

The present invention relates to new unsaturated organometallic compounds derived from titanium and to a process enabling them to be prepared. These new compounds can be applied to the manufacture of new polymers which can in particular form part of the formulation of paints, in particular of marine plants.

SUMMARY OF THE INVENTION

The subject-matter of the present invention is therefore firstly unsaturated organometallic compounds derived from titanium, denoted by the formula (I):

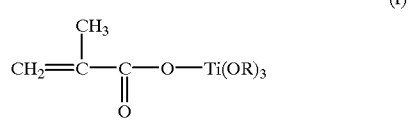

in which R denotes a tert-butyl, tert-amyl or 2-ethyl-hexyl radical.

To prepare the compounds (I) methacrylic acid is reacted with a tetraalkoxytitanium $Ti(OR)_4$, where R=isopropyl or tert-butyl, to obtain the corresponding compound (I), or with $Ti(OR)(OtAm)_3$, where R=isoopropyl or tert-butyl and tAm=tert-amyl, to obtain a compound (I) with R=tert-amyl, the compounds (I) with R=isopropyl or tert-butyl furthermore denoting intermediate synthesis products which can be reacted with tert-amyl alcohol or with 2-ethylhexanol, to obtain a compound (I) in which R denotes tert-amyl or 2-ethylhexyl respectively.

In particular, methacrylic acid is reacted with $Ti(OR)_4$ or $Ti(OR)(OtAm)_3$ with R=isopropyl or tert-butyl and tAm=tert-amyl in stoichiometric conditions at a temperature of 40–80° C., at a pressure of 13.3–66.7 kPa (100–500 mmHg), the methacrylic acid being added to $Ti(OR)4$ or $Ti(OR)(OtAm)_3$, if appropriate in a solvent such as toluene, the alcohol ROH or the ROH-solvent azeotrope released by the reaction being gradually distilled, and, when it is intended to obtain the compound of formula (I) with R=tert-amyl or 2-ethyl-hexyl from the synthesis intermediates, the reaction is continued by introducing tert-amyl alcohol or 2-ethylhexanol into the mixture in a proportion of approximately 3 moles per 1 mole of intermediate compound (I) at a pressure of 13.3–66.7 kPa (100–500 mmHg) and at a temperature of 40–80° C., while distilling the isopropanol or the tert-butanol released by-the reaction.

$Ti(OR)(OtAm)_3$ (R=isopropyl or tert-butyl and tAm=tert-amyl) can be obtained by reacting $Ti(OR)_4$ with tert-amyl alcohol in a proportion of 3 moles of the latter per 1 mole of $Ti(OR)_4$, at a pressure of 13.3–66.7 kPa (100–500 mmHg), at a temperature of 40–80° C., while distilling the isopropanol or tert-butanol released by the reaction.

The following examples illustrate the present invention without, however, limiting its scope.

EXAMPLE 1

Preparation of tri-tert-butoxytitanium methacrylate

Into a 100-ml three-necked round bottom flask equipped with an isobaric dropping funnel, a thermometer and a distillation column are introduced 25.53 g of tetra- tert-butoxytitanium. The reaction is successfully conducted at 18 kPa (135 mmHg), the reaction flask being placed in an oil bath at 55° C. 6.13 g of methacrylic acid are added dropwise with magnetic stirring. The tert-butanol released by the reaction is gradually distilled (boiling point: 41° C./19 kPa (140 mmHg)). The reaction is followed by weighing the distillate released. At the end of the reaction tri-tert-butoxytitanium methacrylate is recovered in the round bottom flask: it is a slightly viscous, pale yellow liquid.

Yield: 97.5%

$^1H$ NMR analysis $\delta_H$ ($C_6D_6$) in ppm:

1.4 [S, 27H, —$CH_3$]

1.7 [s, 3H, —$CH_3$]

5.2 and 6.3 [t, 2H, =$CH_2$].

$^{13}C$ NMR analysis $\delta_c$ ($C_6D_6$) in ppm:

17.0 [—$CH_3$]

32.1 [—$CH_3$]

79.4 [Ti—O—C]

127.2 [=$CH_2$]

136.8 [=C]

185.2 [—$CO_2$—]

IR analysis (film)

2972, 2926 $cm^{-1}$: —$CH_3$ (S)

1645 $cm^{-1}$: C=C (w)

1588, 1525 $cm^{-1}$: —COO— asym (m)

1426 $cm^{-1}$: —COO— sym (m)

1005 $cm^{-1}$: C—O (S, broad)

638 $cm^{-1}$: Ti—O (m)

EXAMPLE 2

Preparation of tri(2-ethylhexoxy)titanium methacrylate

A first stage is conducted, which consists in preparing triisopropoxytitanium methacrylate as synthesis intermediate according to a procedure described in Tr. Inst. Khim., Akad. Nauk. SSR Ural. Filial. 13 39–47 (1968).

The second stage of the synthesis is carried out immediately following the first, at a reduced pressure of 15 kPa (110 mmHg): 19.54 g of 2-ethylhexanol are introduced dropwise with heating and with magnetic stirring, using the second dropping funnel, into the reaction flask containing the synthesis intermediate. The isopropanol released by the reaction is distilled rapidly.

The expected product is recovered in the reaction flask; it is liquid, viscous and pronounced yellow in color.

Yield: 98.5%

$^1$H NMR analysis $\delta_H$ (C$_6$D$_6$) in ppm:

0.9–1.1 [m, 18H, —CH$_3$]

1.1–1.9 [m, 25H, —CH$_2$— and CH]

2.1 [s, 3H, —CH$_3$]

4.6 [t, 6H, —CH$_2$—]

5.4 and 6.5 [t, 2H, =CH$_2$]

$^{13}$C NMR analysis $\delta_c$ (C$_6$D$_6$) in ppm:

11.4 [—CH$_3$]

14.4 [—CH$_3$]

18.9 [—CH$_3$]

23.5 [—CH$_2$—]

23.7 [—CH$_2$—]

29.8 [—CH$_2$—]

30.6 [—CH$_2$—]

43.2 [CH]

79.6 [O—CH$_2$]

124.8 [=CH$_2$]

139.2 [=C]

173.9 [—CO$_2$—]

IR analysis (film):

2958, 2928, 2872 and 2859 cm$^{-1}$: —CH$_2$— and —CH$_3$— (S)

1644 cm$^{-1}$: C=C (w)

1559 cm$^{-1}$: —COO— asym (m)

1423 cm$^{-1}$: —COO— sym (m)

1088 cm$^{-1}$: C—O (m, broad)

673, 618 cm$^{-1}$: Ti—O (m)

EXAMPLE 3

Preparation of tri-tert-amyloxytitanium methacrylate

First stage 14.21 g of tetraisopropoxytitanium are introduced into a 100-ml three-necked round bottom flask equipped with a multiple adaptor with two isobaric dropping funnels, a thermometer and a distillation column. A reduced pressure of 20 kPa (150 mmHg) is then applied to the assembly and the flask is placed in a bath at 55° C. 13.22 g of alcohol are added dropwise with magnetic stirring and the isopropanol released by the reaction is distilled.

Second stare

The second stage of the synthesis is carried out immediately following the first, at a reduced pressure of 20 kPa (150 ammg): 4.30 g of methacrylic acid are introduced dropwise with heating and with magnetic stirring, using the second dropping funnel. The isopropanol released by the reaction is distilled rapidly.

At the end of the reaction the round bottom flask contains a slightly viscous, light yellow liquid.

Yield: 95.8%

$^1$H NMR analysis $\delta_H$ (C$_6$D6) in ppm:

1.0 [t, 9H, —CH$_3$]

1.3 [S, 18H, —CH$_3$]

1.5 [m, 6H, —CH$_2$—]

1.8 [s, 3H, —CH$_3$]

5.2 and 6.3 [t, 2H, =CH$_2$]

$^{13}$C NMR analysis $\delta_C$ (C$_6$D$_6$) in ppm:

9.1 [—CH$_3$]

17.0 [—CH$_3$]

29.6 [—CH$_3$]

37.2 [—CH$_2$—]

80.0 [Ti—O—C]

127.1 [=CH$_2$]

136.8 [=C]

185.1 [—CO$_2$—]

IR analysis (film)

2970, 2926 cm$^{-1}$: —CH$_3$ (S)

1644 cm$^{-1}$: C=C (w)

1587, 1554, 1517 cm$^{-1}$: —COO— asym (m)

1423 cm$^{-1}$: —COO— sym (m)

1003 cm$^{-1}$: C—O (S, broad)

668, 623, 587 cm$^{-1}$: Ti—O (m)

In order to produce polymers from the unsaturated organometallic compounds of this invention, attention is directed to the above cross-referenced application Ser. No. 08/915,931 filed Aug. 21, 1997 for details. It is also seen that the same application contains a disclosure of how to prepare marine antifouling paints from such polymers. Also, it is to be noted that since the unsaturated organometallic compounds of this invention are derivatives of methacrylic acid, one of ordinary skill would know how to polymerize the unsaturated organometallic compounds without even the benefit of the knowledge of the latter application 08/915,799. In other words, one of ordinary skill would use the methods applicable to the polymerization of methyl methacrylate, and make any necessary adjustments thereafter.

The preceding examples can be repeated with similar success by substituting the generically or specifically described reactants and/or operating conditions of this invention for those used in the preceding examples.

The entire disclosure of all applications, patents and publications, cited above, and of corresponding French application No. 96/10372, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. Unsaturated organometallic compound derived from titanium, denoted by the formula (I):

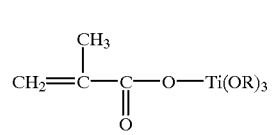

(I)

in which R denotes a tert-butyl, tert-amyl, or 2-ethyl-hexyl radical.

2. A process for manufacture of a compound of formula (I) as defined in claim 1, characterized in that methacrylic acid is reacted with a tetraalkoxytitanium Ti(OR)$_4$, where R=isopropyl or tert-butyl, to obtain a corresponding compound (I), or with Ti(OR) (OtAm)$_3$, where R=isopropyl or tert-butyl and tam=tert-amyl, to obtain a compound (I) with R=tert-amyl, the compounds (I) with R=isopropyl or tert-butyl furthermore denoting intermediate synthesis products which can be reacted with tert-amyl alcohol or with 2-ethylhexanol, to obtain a compound (I) in which R denotes tert-amyl or 2-ethylhexyl respectively.

3. A process according to claim 2, characterized in that methacrylic acid is reacted with Ti(OR)$_4$ or Ti(OR)(OtAm)$_3$ with R=isopropyl or tert-butyl and tAm=tert-amyl in stoichiometric conditions at a temperature of 40–80° C., at a pressure of 13.3–66.7 kPa (100–500 mmHg), the methacrylic acid being added to Ti(OR)$_4$ OR Ti(OR) (OtAm)$_3$, optionally in a solvent, the alcohol ROH or the ROH-solvent azeotrope released by the reaction being gradually distilled, and, when it is intended to obtain the compound of formula (I) with R=tert-amyl or 2-ethylhexyl from synthesis intermediates, the reaction is continued by introducing tert-amyl alcohol or 2-ethylhexanol into the mixture in a proportion of approximately 3 moles per 1 mole of intermediate compound (I) at a pressure of 13.3–66.7 kPa (100–500 mmHg) and at a temperature of 40–80° C., while distilling the isopropanol or the tert-butanol released by the reaction.

4. A process according to claim 3, characterized in that Ti(OR) (OtAm)$_3$ (R=isopropyl or tert-butyl and tAm=tert-amyl) is obtained by reacting Ti(OR)$_4$ with tert-amyl alcohol in a proportion of 3 moles of the latter per 1 mole of Ti(OR)$_4$, at a pressure of 13.3–66.7 kPa (100–500 mmHg) at a temperature of 40–80° C., while distilling the isopropanol or tert-butanol released by the reaction.

5. A compound according to claim 1, wherein R represents tert-butyl.

6. A compound according to claim 1, wherein R represents tert-amyl.

7. A compound according to claim 1, wherein R represents 2-ethylhexyl.

8. A process according to claim 3, wherein the methacrylic acid is added in the presence of a solvent.

9. A process according to claim 8, wherein said solvent is toluene.

* * * * *